(12) United States Patent
Cozzi et al.

(10) Patent No.: US 6,482,920 B1
(45) Date of Patent: Nov. 19, 2002

(54) ACRYLOYL SUBSTITUTED DISTAMYCIN DERIVATIVES, PROCESS FOR PREPARING THEM, AND THEIR USE AS ANTITUMOR AND ANTIVIRAL AGENTS

(75) Inventors: Paolo Cozzi, Milan; Italo Beria, Villamarzana; Giovanni Biasoli, Gavirate; Marina Caldarelli; Laura Capolongo, both of Milan; Cristina Franzetti, Besozzo, all of (IT)

(73) Assignee: Pharmacia Italia, S.p.A., Milan (IT)

( * ) Notice: Subject to any disclaimer, the term of this patent is extended or adjusted under 35 U.S.C. 154(b) by 0 days.

(21) Appl. No.: 09/147,573

(22) PCT Filed: Jul. 10, 1997

(86) PCT No.: PCT/EP97/03719

§ 371 (c)(1), (2), (4) Date: Jan. 22, 1999

(87) PCT Pub. No.: WO98/04524

PCT Pub. Date: Feb. 5, 1998

(30) Foreign Application Priority Data

Jul. 25, 1996 (GB) .............................. 9615692

(51) Int. Cl.$^7$ ................................................. C07K 5/08
(52) U.S. Cl. ........................ 530/331; 530/330; 514/18; 514/19; 548/400
(58) Field of Search ................ 530/330, 331; 514/18, 19; 548/400

(56) References Cited

FOREIGN PATENT DOCUMENTS

| EP | 0246868 | * | 11/1987 |
| GB | 2178036 | * | 2/1987 |
| WO | 90/11277 | * | 10/1990 |

* cited by examiner

Primary Examiner—Christopher S. F. Low
Assistant Examiner—David Lukton
(74) Attorney, Agent, or Firm—Arent Fox Kintner Plotkin & Kahn

(57) ABSTRACT

The present invention relates to acrylol substituted distamycin derivatives, to pharmaceutical compositions comprising such derivatives as well as their use in methods of treating humans and animals, particularly as anti-tumor agents.

10 Claims, No Drawings

ACRYLOYL SUBSTITUTED DISTAMYCIN DERIVATIVES, PROCESS FOR PREPARING THEM, AND THEIR USE AS ANTITUMOR AND ANTIVIRAL AGENTS

The present invention refers to new alkylating antitumor and antiviral agents related to the known antibiotic distamycin A:

which belongs to the family of the pyrroleamidine antibiotics and is reported to interact reversibly and selectively with DNA-AT sequences interfering with both replication and transcription [Nature, 203, 1064 (1964); FEBS Letters, 7 (1970) 90; Prog. Nucleic Acids Res. Mol. Biol., 15, 285 (1975)].

DE-A-1795539 describes the preparation of distamycin derivatives in which the formyl group of distamycin is replaced by hydrogen or by the acid residue of an organic $C_1$–$C_4$ aliphatic acid or of cyclopentylpropionic acid. EP-B-246,868 describes distamycin analogues in which the distamycin formyl group is substituted by aromatic, alicyclic or heterocyclic moieties bearing alkylating. groups.

International patent application WO 90/11277 discloses a broad class of acryloyl substituted distamycin derivatives wherein the acryloyl moiety is linked to the pyrrole ring through a single bond or an aromatic or heterocyclic dicarboxamide group.

It has now been found that a new class of distamycin derivatives as defined hereinunder, wherein the distamycin formyl group is substituted by an acryloyl moiety while the amidine group is substituted by different nitrogen-containing end-groups, shows valuable biological properties.

Accordingly, the present invention relates to new distamycin derivatives of formula (I) as defined hereinunder, to a process for preparing them, to pharmaceutical compositions containing them and to their use in therapy, particularly as antitumor and antiviral agents.

Therefore, object of the present invention are acryloyl substituted distamycin derivatives of formula:

(I)

wherein:
n is 2, 3 or 4;
$R_1$ and $R_2$ are selected, each independently, from: hydrogen, halogen, and $C_4$–$C_4$ alkyl;
$R_3$ is hydrogen or halogen;
B is selected from:

wherein $R_4$, $R_5$, $R_6$, $R_7$, and $R_8$ are, each independently, hydrogen or $C_1$–$C_4$ alkyl, with the proviso that at least one of $R_4$, $R_5$ and $R_6$ is $C_1$–$C_4$ alkyl;
or pharmaceutically acceptable salts thereof.

The present invention includes within its scope also all the possible isomers covered by formula (I) both separately and as a mixture, as well as the metabolites and the pharmaceutically acceptable bio-precursors (otherwise known as pro-drugs) of the compounds of formula (I).

The alkyl groups may have branched or straight chains. A $C_1$–$C_4$ alkyl group is preferably methyl or ethyl. A halogen atom is preferably chlorine, bromine or fluorine. Preferably, $R_4$, R5, $R_6$, $R_7$, and $R_8$ are, each independently, hydrogen, methyl, or ethyl, with the proviso that at least one of $R_4$, $R_5$ and $R_6$ is methyl or ethyl.

Pharmaceutically acceptable salts of the compounds of formula (I) are their salts with pharmaceutically acceptable, either inorganic or organic, acids. Examples of inorganic acids are hydrochloric, hydrobromic, sulfuric and nitric acid; examples of organic acids are acetic, propionic, succinic, malonic, citric, tartaric, methanesulfonic and p-toluenesulfonic acid.

A preferred class of compounds according to the present invention is that of formula (I) wherein:
n is 3 or 4;
$R_1$ and $R_2$ are hydrogen;
$R_3$ is chlorine or bromine;
B is selected from:

wherein $R_4$, $R_5$, R6, $R_7$, and $R_8$ are, each independently, hydrogen or methyl, with the proviso that at least one of $R_4$, $R_5$ and $R_6$ is methyl;
or the pharmaceutically acceptable salts thereof.

Examples of specific compounds according to the present invention, especially in the form of salts, preferably with hydrochloric acid, are the following:

(1) 3-(1-methyl-4-(1-methyl-4-(1-methyl-4-(α-bromo-acrylamido)pyrrole-2-carboxamido)pyrrole-2- carboxamido)pyrrole-2-carboxamido)
propioncyanamidine;

(2) 3-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propioncyanamidine;

(3) 3-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propioncyanamidine;

(4) 3-(1-methyl-4-(1-methyl-4-(1-methyl-4-(α-bromoacrylamido)pyrrole2-carboxamido)pyrrole-2-carboxamido)pyrrole-2-carboxamido)propion-N-methylamidine;

(5) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamidine;

(6) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N-methylamidine;

(7) 3-(1-methyl-4-(1-methyl-4-(1-methyl-4-(α-bromoacrylamido)pyrrole-2-carboxamido)pyrrole-2-carboxamido)pyrrole-2-carboxamido)propion-N,N'-dimethylamidine;

(8) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N'-dimethylamidine;

(9) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N'-dimethylamidine;

(10) 3-(1-methyl-4-(1-methyl-4-(1-methyl-4-(α-bromoacrylamido)pyrrole-2-carboxamido)pyrrole-2-carboxamido)pyrrole-2-carboxamido)propionamidoxime;

(11) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionamidoxime;

(12) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionamidoxime;

(13) 2-(1-methyl-4-(1-methyl-4-(1-methyl-4-(α-bromoacrylamido)pyrrole-2-carboxamido)pyrrole-2-carboxamido)pyrrole-2-carboxamido)ethylguanidine;

(14) 2-(1-methyl-4-(1-methyl-4-(-methyl-4-(1-methyl-4-(α-bromoacrylamido)pyrrole-2-carboxamido)pyrrole-2-carboxamido)pyrrole-2-carboxamido)pyrrole-2-carboxamido)ethylguanidine;

(15) 2-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)ethylguanidine;

(16) 3-(1-methyl-4-(1-methyl-4-(1-methyl-4-(α-bromoacrylamido)pyrrole-2-carboxamido)pyrrole-2-carboxamido)pyrrole-2-carboxamido)propionitrile;

(17) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionitrile;

(18) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionitrile;

(19) 3-(1-methyl-4-(1-methyl-4-(1-methyl-4-(α-bromoacrylamido)pyrrole-2-carboxamido)pyrrole-2-carboxamido) pyrrole-2-carboxamido)propionamide;

(20) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionamide;

(21) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionamide;

(22) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamide;

(23) 3-(1-methyl-4-(1-methyl-4-(1-methyl-4-(α-bromoacrylamido)pyrrole-2carboxamido)pyrrole-2-carboxamido)pyrrole-2-carboxamido)propion-N,N-dimethylamidine;

(24) 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N-dimethylamidine;

(25) 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N-dimethylamidine;

(26) 3-(1-methyl-4-(1-methyl-4-(1-methyl-4-(α-chloroacrylamido)pyrrole-2-carboxamido)pyrrole-2-carboxamido)pyrrole-2-carboxamido)propion-N-methyl-amidine;

(27) 3-(1-methyl-4-(1-methyl-4-(α-methyl-4-(α-chloroacrylamido)pyrrole-2-carboxamido) pyrrole-2-carboxamido)pyrrole-2-carboxamido)propion-N,N'-dimethyl-amidine;

(28) 3-(1-methyl-4-(1-methyl-4-(1-methyl-4-(α-chloroacrylamido)pyrrole-2-carboxamido)pyrrole-2-carboxamido)pyrrole-2-carboxamido)propionamidoxime;

(29) 3-(1-methyl-4-(1-methyl-4-(1-methyl-4-(α-chloroacrylamido)pyrrole-2-carboxamido)pyrrole-2-carboxamido)pyrrole-2-carboxamido)propioncyanamidine; and

(30) 3-(1-methyl-4-(1-methyl-4-(1-methyl-4-(α-chloroacrylamido)pyrrole-2-carboxamido)pyrrole-2-carboxamido)pyrrole-2-carboxamido)propionamide.

The compounds of formula (I) and the salts thereof, object of the present invention, can be prepared according to one of the following processes, which comprise:

(a) reacting a compound of formula:

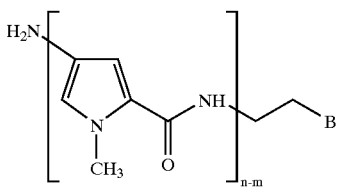
(II)

wherein:
n is 2, 3 or 4;
m is 0 or 1;
B is selected from:

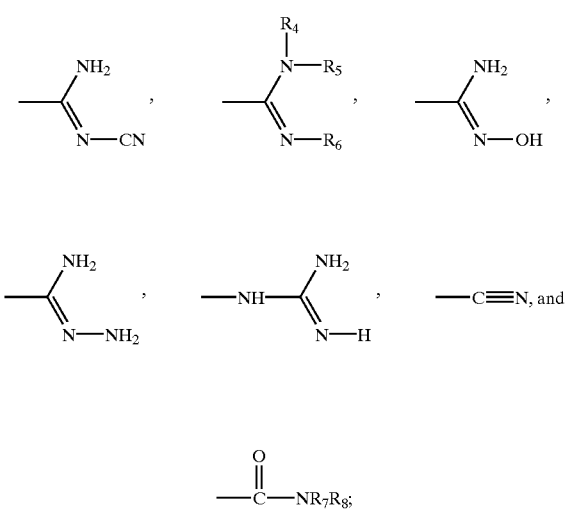

wherein $R_4$, $R_5$, $R_6$, $R_7$, and $R_8$ are, each independently, hydrogen or $C_1$–$C_4$ alkyl, with the proviso that at least one of $R_4$, $R_5$ and $R_6$ is $C_1$–$C_4$ alkyl;
with a compound of formula:

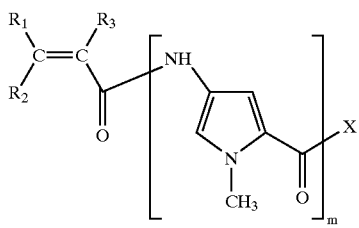
(III)

wherein: $R_1$ and $R_2$ are selected, each independently, from: hydrogen, halogen, and $C_1$–$C_4$ alkyl; $R_3$ is hydrogen or halogen; X is hydroxy or a leaving group; and m has the above reported meanings;

or:

(b) when B is equal to —C≡N, reacting a compound of formula:

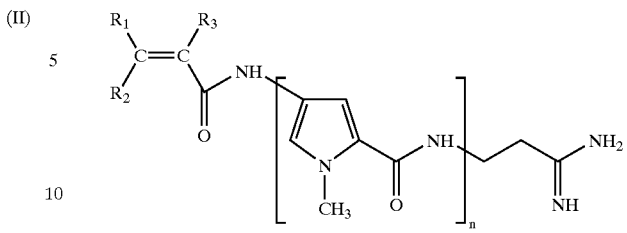
(IV)

wherein n, $R_1$, $R_2$, and $R_3$ are as defined above;
with succinic anhydride, and, if desired, converting a compound of formula (I) into a pharmaceutically acceptable salt thereof.

In the compounds of formula (III), X is hydroxy or a leaving group selected, for instance, from chloro, 2,4,5-trichlorophenoxy, 2,4-dinitro-phenoxy, succinimido-N-oxy, imidazolyl group, and the like.

The reaction of process (a) between a compound of formula (II) and a compound of formula (III) can be carried out according to known methods, for instance those described in EP-B-246,868.

The reaction between a compound of formula (II) and a compound of formula (III) wherein X is hydroxy, is preferably carried out with a molar ratio (II):(III) of from 1:1 to 1:2, in an organic solvent, such as, e.g., dimethylsulfoxide, hexamethylphosphotriamide, dimethyl-acetamide, dimethyl-formamide, ethanol, benzene, or pyridine, in the presence of an organic or inorganic base such as, e.g., triethylamine, diisopropyl ethylamine, or sodium or potassium carbonate or bicarbonate, and of a condensing agent such as, e.g., N-ethyl-N'-(3-dimethylamino-propyl)-carbodiimide, N,N'-dicyclo-hexylcarbodiimide, and/or 1-hydroxy-benzotriazole hydrate. The reaction temperature may vary from about –10° C. to about 100° C., and the reaction time from about 1 to about 24 hours.

The reaction between a compound of formula (II) and a compound of formula (III), wherein X is a leaving group as defined above, may be carried out with a molar ratio (II):(III) of from about 1:1 to about 1:2, in an organic solvent, such as, e.g., dimethylformamide, dioxane, pyridine, benzene, tetrahydrofurane, or mixtures thereof with water, optionally in the presence of an organic base, e.g. N,N'-diisopropylethylamine, triethylamine, or an inorganic base, e.g. sodium or potassium bicarbonate, at a temperature of from about 0° C. to about 100° C., and for a time varying from about 2 hours to about 48 hours. The optional conversion of a compound of formula (I) into a pharmaceutically acceptable salt thereof may be carried out by conventional known method.

The compounds of formula (II) are known compounds, or can be obtained by known methods (see e.g. Tetrahedron Letters 31, 1299 (1990), Anti cancer Drug Design 9, 511 (1994)), such as:

(i) by hydrolitic deformylation, in a basic or acid medium, of compounds of formula:

$$[\text{H-C(=O)-NH-pyrrole(N-CH}_3\text{)-C(=O)-NH-(CH}_2)_n\text{-B}]_{n-m} \quad (V)$$

or (ii) by nitro-group reduction, according to known methods, of compounds of formula:

$$[\text{O}_2\text{N-pyrrole(N-CH}_3\text{)-C(=O)-NH-(CH}_2)_n\text{-B}]_{n-m} \quad (VI)$$

wherein in the compounds of formula (V) and (VI):
n is 2, 3 or 4; m is 0 or 1;
is selected from:

$$\begin{array}{c} \text{—C(=NH)—NH—CN}, \quad \text{—C(=NR}_4\text{)—N(R}_5\text{)(R}_6\text{)}, \quad \text{—C(=NH)—NH—OH}, \\ \text{—C(=NH)—NH—NH}_2, \quad \text{—NH—C(=NH)—NH}_2, \quad \text{—C}\equiv\text{N, and} \\ \text{—C(=O)—NR}_7\text{R}_8; \end{array}$$

wherein $R_4$, $R_5$, $R_6$, $R_7$, and $R_8$ are, each independently, hydrogen or $C_1$–$C_4$ alkyl, with the proviso that at least one of $R_4$, $R_5$ and $R_6$ is $C_1$–$C_4$ alkyl.

The compounds of formula (V), except when B is equal to $$\text{—NH—C(=NH)—NH}_2,$$

can in turn be prepared starting from distamycin analogues of formula:

$$[\text{H-C(=O)-NH-pyrrole(N-CH}_3\text{)-C(=O)-NH-(CH}_2)_n\text{-C(=NH)NH}_2]_{n-m} \quad (VII)$$

by using:

(i) $H_2N$—CN, so obtaining a compound of formula (I) having B equal to:

$$\text{—C(NH}_2\text{)=N—CN};$$

(ii) $H_2N$—OH, so obtaining a compound of formula (I) having $$\text{—C(NH}_2\text{)=N—OH};$$

(iii) $H_2N$—$NH_2$, so obtaining a compound of formula (I) having B equal to:

$$\text{—C(NH}_2\text{)=N—NH}_2;$$

(iv) $HNR_4R_5$, so obtaining a compound of formula (I) having B equal to:

$$\text{—C(=NH)—N(R}_4\text{)(R}_5\text{)};$$

and then optionally with $H_2NR_6$, so obtaining a compound of formula (I) having B equal to:

$$\text{—C(=N—R}_6\text{)—N(R}_4\text{)(R}_5\text{)};$$

wherein $R_4$, $R_5$, and $R_6$ are, each independently, hydrogen or $C_1$–$C_4$ alkyl, with the proviso that at least one of $R_4$, $R_5$, and $R_6$ is $C_1$–$C_4$ alkyl;

(v) succinic anhydride, so obtaining a compound of formula (I) having B equal to —C≡N;

(vi) water in an alkaline medium, so obtaining a compound of formula (I) having B equal to —CO—$NR_7R_8$ wherein $R_7$ and $R_8$ are both hydrogen; (vii) $HNR_7R_8$, so obtaining a compound of formula (I) having B equal to:

$$\text{—C(=NH)—N(R}_7\text{)(R}_8\text{)};$$

and then with water in an alkaline medium, so obtaining a compound of formula (I) having B equal to —CO—$NR_7R_8$, wherein $R_7$ and $R_8$ are, each independently, hydrogen or $C_1$–$C_4$ alkyl, with the proviso that at least one of $R_7$ and $R_8$ is $C_1$–$C_4$ alkyl.

The reaction between a compound of formula (VII) and one of the reactants as described at points (i), (ii), (iii), (iv), or (vii) can be carried out according to known methods, for instance those reported in: U.S. Pat. No. 4,766,142, Chem. Revs. 1961, 155; J. Med. Chem. 1984, 27, 849–857; Chem. Revs. 1970, 151; and "The Chemistry of Amidines and Imidates", edited by S. Patai, John Wiley & Sons, N.Y. (1975).

The reaction of a compound of formula (VII) with succinic anhydride (see point (v) above) is preferably carried out with a molar ratio (VII):succinic anhydride of from 1:1 to 1:3 in an organic solvent such as, e.g., dimethylsulfoxide, dimethylformamide, in the presence of an organic or inorganic base such as, e.g., triethylamine, diisopropylethylamine, sodium or potassium carbonate, and the like. The reaction temperature may vary from about 25° C. to about 100° C., and the reaction time from about 1 hour to about 12 hours.

The reaction with water in an alkaline medium (see points (vi) and (vii) above) may be carried out according to known methods usually employed for an alkaline hydrolysis, e.g. by treating the substrate with an excess of sodium or potassium hydroxide dissolved in water or in a mixture of water with an organic solvent, e.g. dioxane, tetrahydrofurane, or acetonitrile, at a temperature of from about 50° to about 100° C., for a time varying from about 2 hours to about 48 hours.

The compounds of formula (III) are known compounds or may be prepared starting from known compounds through reactions well known in organic chemistry: see, for instance, J.C.S. 1947–1032 and JACS 62, 3495 (1940).

The compounds of formula (VI) can be obtained:

(i) except when B is equal to

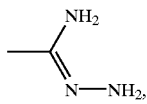

from a compound of formula:

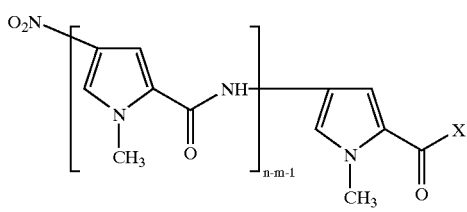

(VIII)

wherein n, m and X are as defined above, by reaction with a compound of formula:

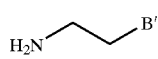

(IX)

wherein B' is selected from:

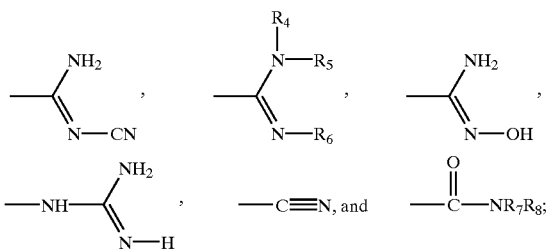

(ii) except when B is equal to

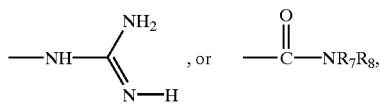

Pinner reaction of a compound of formula:

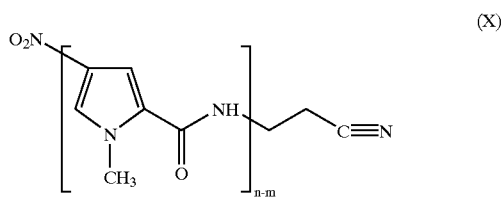

(X)

with a suitable amine compound as defined at point (i), (ii), (iii) or (iv) above.

The compounds of formulas (VII), (VIII), (IX) and (X) are known compounds, or may be obtained by known methods (see e.g. Tetrahedron, 34, 2389–2391, 1978; J. Org. Chem., 46, 3492–3497, 1981).

The reaction of process (b) is preferably carried out with a molar ratio (IV):succinic anhydride of from 1:1 to 1:3 in an organic solvent such as, e.g., dimethylsulfoxide or dimethylformamide, in the presence of an organic or inorganic base such as, e.g., triethylamine, diisopropylethylamine, sodium or potassium carbonate, and the like. The reaction temperature may vary from about 25° C. to about 100° C., and the reaction time from about 1 hour to about 12 hours.

The compounds (IV) can be obtained with known methods, for example, those described in WO 90/11277.

Salification of a compound of formula (I), as well as preparation of a free compound starting from a salt, may be carried out by known standard methods.

Well known procedures such as, e.g., fractional crystallization or chromatography, may also be followed for separating a mixture of isomers of formula (I) into the single isomers.

The compounds of formula (I) may be purified by conventional techniques such as, e.g., silica gel or alumina column chromatography, and/or by recrystallization from an organic solvent such as, e.g., a lower aliphatic alcohol, e.g. methyl, ethyl or isopropyl alcohol, or dimethylformamide.

PHARMACOLOGY

The compounds of formula (I) according to the present invention are useful as antineoplastic and antiviral agents.

Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity was evaluated by cytotoxicity studies carried out on murine $L_{1210}$ leukemia cells. Cells were derived from in vivo tumors and established in cell culture. Cells were used until the tenth passage. Cytotoxicity was determined by counting surviving cells after 48 hours treatment.

The percentage of cell growth in the treated cultures was compared with that of controls. $IC_{50}$ values (concentration inhibiting 50% of the cellular growth in respect to controls) were calculated on dose-response.

The compounds of the invention were tested also in vivo on $L_{1210}$ murine leukemia and on murine reticulosarcoma M 5076, showing a very good antitumoral activity, with the following procedure.

$L_{1210}$ murine leukemia was maintained in vivo by i.v. serial transplantation. For experiments, $10^5$ cells were injected i.p. in CD2F1 female mice, obtained from Charles River Italy Animals were 8 to 10 weeks old at the beginning of the experiments. Compounds were administered i.v. at day +1 after tumor cells injections.

M5076 reticulosarcoma was maintained in vivo by i.m. serial transplantation. For experiments, $5+10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection.

Survival time of mice and tumor growth were calculated and activity was expressed in term of T/C % and T.I. %.

$$T/C = \frac{\text{median survival time treated group}}{\text{median survival time untreated group}} \times 100$$

T.I. = % inhibition of tumor growth respect to control

Tox: number of mice which died for toxicity. Tox determination was made when mice died before the control and/or tested significant body weight loss and/or spleen and/or liver size reduction were observed.

The compounds of the invention show also a remarkable effectiveness in interfering with the reproductive activity of pathogenic viruses and protect tissue cells from viral infections. For example, they show activity against DNA viruses such as, for instance, herpes, e.g. herpes simplex and herpes zoster viruses, virus vaccinia, RNA viruses such as, e.g., Rhinovirus and Adenovirus, and against retroviruses such as, for instance, sarcoma viruses, e.g., urine sarcoma virus, and leukemia viruses, e.g. Friend leukemia virus.

For example, effectiveness against herpes, coxsackie and respiratory syncytial viruses was tested in a fluid medium as follows. Serial two-fold dilutions of the compounds from 200 to 1.5 mcg/ml were distributed in duplicate 0.1 ml/well in 96 well microplates for tissue culture. Cell suspensions ($2\times10^5$ cells/ml) infected with about $5\times10^{-3}$ $TCID_{50}$ of virus/cell were immediately added 0.1 ml/well.

After 3–5 day incubation at 37° C. in $CO_2$ 5%, the cell cultures were evaluated by microscope observation and Minimum Inhibiting Concentration (MIC) was determined, MIC being the minimum concentration which determines a reduction of cytopathic effect in comparison with the infected controls.

The compounds of the invention can be administered to mammals, including humans, through the usual routes, for example, parenterally, e.g. by intravenous injection or infusion, intramuscularly, subcutaneously, topically or orally. The dosage depends on the age, weight and conditions of the patient and on the administration route. For example, a suitable dosage for administration to adult humans may range from about 0.1 to about 150–200 mg pro dose 1–4 times a day.

Further object of the present invention are pharmaceutical compositions, which comprise a compound of formula (I) as an active principle, in association with one or more pharmaceutically acceptable carrier and/or diluent.

The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulfates; and, in general, non-toxic and pharmacologically inactive substances used in pharmaceutical formulation. Said pharmaceutical preparation may be manufactered by known techniques, for example by means of mixing, granulating, tabletting, sugar-coating or film-coating processes.

A further object of the present invention are the compounds of formula (I) for use in a method for treating the human or animal body by therapy.

Furthermore, the present invention provides a method for treating tumors and viral infections in a patient in need of it, which comprises administering to said patient a composition of the invention.

A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides combined preparations for simultaneous, separate or sequential use in anti-cancer therapy, comprising a compound of formula (I), or a pharmaceutically acceptable salt thereof, and an additional antitumour agent.

The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluoro-uracil, melphalan, cyclo-phosphamide, 4-demethoxy daunorubicin, bleomycin, vinblastin, and mitomycin, or mixtures thereof.

The following examples are given to better illustrate the invention, but do not limit the scope of the invention itself.

EXAMPLE 1

3-[1-Methyl-4[1-methyl-4[1-methyl-4[1-methyl-4(α-bromo-acrylamido)pyrrole-2-carboxamido]pyrrole-2-carboxamido]pyrrole-2-carboxamido]pyrrole-2-carboxamido]propion-cyanamidine Step I The Intermediate 3-[1-Methyl-4[1-methyl-4[1-methyl-4-aminopyrrole-2-carboxamido]pyrrole-2-carboxamido]pyrrole-2-carboxamido]propioncyanamidine Hydrochloride To a solution of 324 mg of cyanamide in 20 ml of DMF were added 186 mg of sodium hydride. The mixture was stirred at room temperature for 30 min and then added to a solution of 1 g of distamycin A in 10 ml DMF. The solution was stirred at room temperature for two hours, then acetic acid was added until pH=7. The solvent was removed at reduced pressure and the crude residue purified by flash chromatography (methylene chloride/methanol: 9/1) to give 900 mg of 3-[1-methyl-4[1-methyl-4[1-methyl-4-formamido-pyrrole-2-carboxamido]pyrrole-2-carboxamido] pyrrole-2-carboxamido]propioncyanamidine which was dissolved in 50 ml of methanol and added of 5 ml of 2N hydrochloric acid. The reaction was stirred at room temperature for two days, solvent evaporated in vacuo and the solid residue suspended in 200 ml of ethyl acetate, yielding after filtration 600 mg of the intermediate.

FAB-MS: m/z 479, (65, [M+H]$^+$); PMR (DMSO-d$_6$) δ: 10.11 (s, 1H), 9.97 (s, 1H), 9.80–9.60 (b.s., 2H), 8.50–8.00 (b.s., 3H), 7.40 (t, J=5.8 Hz, 1H), 7.25 (d, J=1.7 Hz, 1H), 7.19 (d, J=1.7 Hz, 1H), 7.08 (d, J=1.7 Hz, 1H), 7.06 (d, J=1.7 Hz, 1H), 6.94 (d, J=1.7 Hz, 1H), 6.88 (d, J=1.7 Hz, 1H), 3.81 (s, 3H), 3.79 (s, 3H), 3.75 (s, 3H), 3.41 (m, 2H), 2.70 (m, 2H).

Step II The Intermediate 1-Methyl-4-(α-bromoacrylamido)pyrrole-2-carboxyl Chloride To a solution of α-bromoacrylic acid (1.7 g) in dry CH$_3$CN (5 ml) a solution of N,N'-dicycloexylcarbodiimide (1.2 g) in 20 ml CH$_3$CN was added in 1 hour and the resulting suspension was stirred at 25° C. for 20'. The white precipitate was filtered and the resulting solution was added to a solution of 1-methyl-4-aminopyrrole-2-carboxylic acid hydrochloride (1 g) in 20 ml of H$_2$O and 1.4 g of NaHCO$_3$. The solution was stirred for 1 hour at 25° C. then HCl 2N was added until pH=3. The solvent was removed at reduced pressure and the crude residue purified by flash chromatography (methylene chloride/methanol: 95/5) to give 1.2 g of 1-methyl-4-(α-bromoacrylamido)pyrrole-2-carboxylic acid, which was dissolved in benzene (40 ml) and added of 10 ml of SOCl$_2$. The solution was refluxed for 1 hour then evaporated to dryness in vacuo to give 1.4 g of the intermediate.

By analogous procedure and by using the opportune starting materials the following product can be obtained: 1-methyl-4-(α-chloroacrylamido)pyrrole-2-carboxyl chloride.

Step III The Title Compound

To a solution of 206 mg of the intermediate obtained from step I, 100 mg of NaHCO$_3$ in 40 ml of water and 20 ml of dioxane, a solution of 175 mg of the intermediate obtained from step II in 40 ml of dioxane was added. The solution was stirred for 2 hours at 25° C. then the solvent evaporated in vacuo and the crude residue purified by flash chromatography (methylene chloride/methanol: 10/1) to yield 150 mg of the title compound as a yellow solid.

FAB-MS: m/z 732, (42, [M–H]$^-$); PMR (DMSO-d$_6$ 45° C.) δ: 10.27 (s, 1H), 9.95 (s, 1H), 9.92 (s, 1H), 9.88 (s, 1H), 8.3 (b.s., 2H), 8.1 (b.s., 1H), 6.8–7.3 (m, 8H), 6.67 (d, J=2.9 Hz, 1H), 6.22 (d, J=2.9 Hz, 1H), 3.85 (s, 6H), 3.84 (s, 3H), 3.79 (s, 3H), 3.45 (b.s., 2H), 2.6 (b.s., 2H).

By analogous procedure and by using the opportune starting materials the following products can be obtained:

3-[1-methyl-4[1-methyl-4[1-methyl-4-(α-bromoacrylamido)pyrrole-2-carboxamido)pyrrole-2-carboxamido]pyrrole-2-carboxamido] propioncyanamidine; and 3-[1-methyl-4[1-methyl-4[1-methyl-4(α-chloroacrylamido)pyrrole-2-carboxamido]pyrrole-2-carboxamido]pyrrole-2-carboxamido]propioncyanamidine.

EXAMPLE 2

3-[1-Methyl-4[1-methyl-4[1-methyl-4[1-methyl-4-(α-bromoacrylamido)pyrrole-2-carboxamido]pyrrole-2-carboxamido]pyrrole-2-carboxamido]pyrrole-2-carboxamido]propion-N-methyl-amidine Hydrochloride Step I The Intermediate 3-[1-Methyl-4[1-methyl-4[1-methyl-4-aminopyrrole-2-carboxamido]pyrrole-2-carboxamido]pyrrole-2-carboxamido]propion-N-methyl-amidine Dihydrochloride A solution of 2 g of distamycin A in 50 ml DMF was treated with 0.38 ml of methylamine hydrochloride 80%. After 8 hours additional 0.25 equivalent of methylamine hydrochloride 80% was added. The solution was evaporated to dryness and the crude residue was purified by flash chromatography (methylene chloride/methanol: 8/2) to give 1.5 g of 3-[1-methyl-4[1-methyl-4[1-methyl-4-formamidopyrrole-2-carboxamido)pyrrole-2-carboxamido] pyrrole-2-carboxamido]propion-N-methyl-amidine hydrochloride which was dissolved in 40 ml of methanol and added of 5 ml of 2N hydrochloric acid.

The reaction was stirred at room temperature for two days, the solvent evaporated in vacuo and the solid residue suspended in 200 ml of ethyl acetate, yielding after filtration 1.4 g of the intermediate.

FAB-MS: m/z 468, (40, [M+H]⁺); PMR (DMSO-d₆) δ: 10.20 (s, 3H), 10.18 (s, 1H), 9.65 (m, 1H), 9.20 (s, 1H), 8.63(s, 1H), 8.25 (t, J=5.8 Hz, 1H), 7.25 (d, J=1.7 Hz, 1H), 7.19 (d, J=1.7 Hz, 1H), 7.11 (d, J=1.7 Hz, 1H) 7.08 (d, J=1.7 Hz, 1H), 7.05 (d, J=1.7 Hz, 1H), 6.91 (d, J=1.7 Hz, 1H), 3.90 (s, 3H), 3.85 (s, 3H), 3.79 (s, 3H), 3.60–3.40 (m, 2H), 2.80 (d, J=6 Hz, 3H), 2.61 (m, 2H).

By analogous procedure and by using the opportune starting material the following product can be obtained:

3-[1-methyl-4[1-methyl-4[1-methyl-4-aminopyrrole-2-carboxamido)pyrrole-2-carboxamido]pyrrole-2-carboxamido]propion-N,N-dimethyl-amidine dihydrochloride.

Step II The Title Compound

A solution of 170 mg of 1-methyl-4-(α-bromoacrylamido)pyrrole-2-carboxyl chloride (prepared as reported in Example 1 step II) in 30 ml of dioxane, was added to a solution of the intermediate obtained from step I (162 mg) and 75 mg of NaHCO₃ in 25 ml of H₂O. The solution was stirred for 2 hours at room temperature, acidified with HCl 2N until pH=5 and then evaporated in vacuo. The crude residue was purified by flash chromatography (methylene chloride/methanol: 8/2) to yield 120 mg of the title compound as a yellow solid.

FAB-MS: m/z 722, (18, [M+H]⁺); PMR (DMSO-d₆) δ: 10.34 (s, 1H), 9.98 (s, 1H), 9.95 (s, 1H), 9.92 (s, 1H), 9.5 (b.s., 1H), 9.1 (b.s., 1H), 8.5 (b.s., 1H), 8.22 (t, J=5.9 Hz, 1H), 6.9–7.3 (m, 8H), 6.68 (d, J=2.8 Hz, 1H), 6.22 (d, J=2.8 Hz, 1H), 3.85 (s, 6H), 3.84 (s, 3H), 3.80 (s, 3H), 3.48 (b.s., 2H), 2.79 (s, 3H), 2.62 (b.s., 2H).

By analogous procedure and by using the opportune starting materials the following products can be obtained:

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N-dimethylamidine hydrochloride.

FAB-MS: m/z 736, (100, [M+H]⁺); PMR (DMSO-d₆) δ: 10.37 (s, 1H), 9.99 (s, 1H), 9.95 (s, 1H), 9.94 (s, 1H), 9.0 (b.s., 1H), 8.3 (b.s., 1H), 8.31 (t, J=5.8 Hz, 1H), 6.9–7.3 (m, 8H), 6.70 (d, J=2.9 Hz, 1H), 6.22 (d, J=2.9 Hz, 1H), 3.84 (s, 6H), 3.83 (s, 3H), 3.80 (s, 3H), 3.46 (m, 2H), 3.22 (b.s., 3H), 3.03 (b.s., 3H), 2.77 (t, J=6.5 Hz, 2H);

3-[1-methyl-4[1-methyl-4-(1-methyl-4-(α-bromoacrylamido)pyrrole-2-carboxamido]pyrrole-2-carboxamido]pyrrole-2-carboxamido]propion-N-methyl-amidine hydrochloride;

3-[1-methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propion-N-methyl-amidine hydrochloride;

3-(1-methyl-4-(1-methyl-4-(1-methyl-4-(α-bromoacrylamido)pyrrole-2-carboxamido)pyrrole-2-carboxamido)pyrrole-2-carboxamido)propion-N,N-dimethylamidine hydrochloride; and 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N-dimethylamidine hydrochloride.

EXAMPLE 3

3-[1-Methyl-4[1-methyl-4[1-methyl-4-(1-methyl-4-(α-bromoacrylamido)pyrrole-2-carboxamido]pyrrole-2-carboxamido]pyrrole-2-carboxamido]pyrrole-2-carboxamido]propion-N,N'-dimethyl-amidine Hydrochloride Step I The Intermediate 3-[1-Methyl-4[1-methyl-4[1-methyl-4-aminopyrrole-2-carboxamido]pyrrole-2-carboxamido]pyrrole-2-carboxamido]propion-N,N'-dimethyl-amidine Dihydrochloride A solution of 1.5 g of distamycin A in 40 ml DMF was heated at 80° C. and treated with 4 ml of methylamine hydrochloride 80%. After 4 hours additional 5 equivalent (4 ml) of methylamine hydrochloride 80% were added. The solution was evaporated to dryness and the crude residue was purified by flash chromatography (methylene chloride/methanol: 8/2) to give 1.2 g of 3-[1-methyl-4[1-methyl-4[1-methyl-4-formamidopyrrole-2-carboxamido]pyrrole-2-carboxamido]pyrrole-2-carboxamido]propion-N,N'-dimethyl-amidine hydrochloride which was dissolved in 40 ml of methanol and added of 5 ml of 2N hydrochloric acid solution.

The reaction was stirred at room temperature for two days, the solvent evaporated in vacuo and the solid residue suspended in 200 ml of ethyl acetate, yielding after filtration 1.4 g of the intermediate.

FAB-MS: m/z 482, (45, [M+H]⁺); PMR (DMSO-d₆) δ; 10.21 (s, 3H), 10.18 (s, 1H), 9.61 (m, 1H), 8.85 (s, 1H) 8.39 (t, J=5.8 Hz, 1H), 8.00–7.70 (b.s., 1H), 7.28 (d, J=1.7 Hz, 1H), 7.22 (d, J=1.7 Hz, 1H), 7.12 (d, J=1.7 Hz, 1H) 7.08 (d, J=1.7 Hz, 1H), 7.03 (d, J=1.7 Hz, 1H), 6.92 (d, J=1.7 Hz, 1H), 3.92 (s, 3H), 3.89 (s, 3H), 3.86 (s, 3H), 3.60–3.40 (m, 2H), 3.02 (d, J=6 Hz, 3H), 2.80 (d, J=6 Hz, 3H), 2.72 (m, 2H).

Step II The Title Compound

A solution of 200 mg 1-methyl-4-(α-bromoacrylamido)pyrrole-2-carboxyl chloride (prepared as reported in Example 1 step II) in 10 ml of benzene, was added to a solution of the intermediate obtained from step I (250 mg) and 76 mg of NaHCO₃ in 5 ml of H₂O . The solution was stirred for 1 hour at room temperature, then evaporated under reduced pressure and the crude residue was purified by flash chromatography (methylene chloride/methanol: 85/15) to yield 185 mg of the title compound as a yellow solid.

FAB-MS: m/z 736, (70, [M+H]⁺); PMR (DMSO-d6) δ: 10.38 (s, 1H), 10.00 (s, 1H), 9.96 (s, 1H), 9.94 (s, 1H), 9.2 (b.s., 2H), 8.33 (t, J=6.0 Hz, 1H), 6.9–7.3 (m, 8H), 6.71 (d, J=2.9 Hz, 1H), 6.22 (d, J=2.9 Hz, 1H), 3.85 (s, 6H), 3.84 (s, 3H), 3.80 (s, 3H), 3.44 (b.s., 2H),3.00 (s, 3H), 2.79 (s, 3H), 2.73 (b.s., 2H). UV: c=18.1 mg/l(EtOH 95%) $\lambda_{MAX}$=312 ε=44375.

By analogous procedure and by using the opportune starting materials the following products can be obtained:

3-[1-methyl-4[1-methyl-4[1-methyl-4-(α-bromoacrylamido)pyrrole-2-carboxamido]pyrrole-2-carboxamido]pyrrole-2-carboxamido]propion-N,N'-dimethyl-amidine hydrochloride; and 3-[1-methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propion-N,N'-dimethyl-amidine hydrochloride.

EXAMPLE 4

3-[1-Methyl4[1-methyl-4[1-methyl-4[1-methyl-4-(α-bromo-acrylamido)pyrrole-2-carboxamido]pyrrole-2- carboxamido]pyrrole-2-carboxamido]pyrrole-2-carboxamido]propionamidoxime

Step I The Intermediate 3-[1-Methyl-4[1-methyl-4-(1-methyl-4-aminopyrrole-2-carboxamido]pyrrole-2-carboxamido]pyrrole-2-carboxamido]propionamidoxime Hydrochloride A solution of 2 g of distamycin A in 35 ml DMF was heated to 80° C. and treated with 0.46 ml of hydroxylamine 1M in DMF. After 30' additional 1 equivalent of hydroxylamine 1M in DMF was added. The solution was evaporated to dryness and the crude residue was purified by flash chromatography (methylene chloride/methanol: 9/1) to give 1.50 g of 3-[1-methyl-4[1-methyl-4[1-methyl-4-formamidopyrrole-2-carboxamido]pyrrole-2-carboxamido]pyrrole-2-carboxamido]propionamidoxime which was dissolved in 50 ml of methanol and added of 10 ml of HCl 2N. The solution was stirred at room temperature for 2 days, the solvent evaporated in vacuo and the solid residue suspended in 200 ml of ethyl acetate, yielding, after filtration 1.4 g of the intermediate.

FAB-MS: m/z 480 (20, [M+H]$^+$); PMR (DMSO-d$_6$) δ: 10.18 (b.s., 3H); 9.98 (s, 1H); 8.32 (t, J=5.7 Hz, 1H); 7.25 (d, J=1.7 Hz, 1H); 7.20 (d, J=1.7 Hz, 1H); 7.16 (d, J=1.7 Hz, 1H); 7.12 (d, J=1.7 Hz, 1H); 7.10 (d, J=1.7 Hz, 1H); 6.93 (d, J=1.7 Hz, 1H); 3.89 (s, 3H); 3.86 (s, 3H) 3.82 (b.s., 7H); 3.50 (m, 2H); 2.22 (m, 2H).

Step II The Title Compound

To a solution of 277 mg of the intermediate obtained from step I and 137 mg of NaHCO$_3$ in 55 ml of H$_2$O, a solution of 203 mg of 1-methyl-4-(α-bromoacrylamido)pyrrole-2-carboxyl chloride (prepared as reported in Example 1 step II) in 55 ml of dioxane, was added. The solution was stirred for 5 hours at room temperature, then evaporated in vacuo and the crude residue was purified by flash chromatography (methylene chloride/methanol: 85/15) to yield 90 mg of the title compound as a hazel solid.

FAB-MS: m/z 724, (10, [M+H]$^+$); PMR (DMSO-d$_6$) δ: 10.27 (s, 1H), 9.94 (s, 1H), 9.91 (s, 1H), 9.88 (s, 1H), 9.5 (b.s., 2H), 8.5 (b.s., 1H), 7.98 (t, J=5.9 Hz, 1H), 7.3–6.8 (m, 8H), 6.66 (d, J=2.9 Hz, 1H), 6.21 (d, J=2.9 Hz, 1H), 3.84 (s, 6H), 3.83 (s, 3H), 3.79 (s, 3H), 3.38 (b.s., 2H), 2.31 (b.s., 2H). UV: c=4.16 mg/l(MeOH) $\lambda_{MAX}$=307.8 ϵ=51155.

By analogous procedure and by using the opportune starting materials the following products can be obtained:

3-[1-methyl-4[1-methyl-4[1-methyl-4-(α-bromoacrylamido)pyrrole-2-carboxamido]pyrrole-2-carboxamido]pyrrole-2-carboxamido]propionamidoxime; and 3-[1-methyl-4[1-methyl-4[1-methyl-4-(α-chloroacrylamido)pyrrole-2-carboxamido]pyrrole-2-carboxamido]pyrrole-2-carboxamido]propionamidoxime.

EXAMPLE 5

2-[1-Methyl-4[1-methyl-4[1-methyl-4[1-methyl-4-(α-bromo-acrylamido)pyrrole-2-carboxamido]pyrrole-2-carboxamido]pyrrole-2-carboxamido]pyrrole-2-carboxamido]ethylguanidine Hydrochloride Step I The Intermediate 2-Aminoethylguanidine Dihydrochloride A solution of commercial N-BOC-ethylendiamine (1 g) in dry ethanol (100 ml) and 2-methyl-2-thiopseudourea hydroiodide (1.5 g) was refluxed for 8 hours. The solvent was removed at reduced pressure and the crude residue purified by flash chromatography (methylene chloride/methanol: 9/1) to yield 1.5 g of N-BOC-2-aminoethylguanidine hydroiodide as a yellow oil which was dissolved in methanolic hydrochloric acid solution 5N (20 ml) and stirred at room temperature for 3 hours. The white precipitate was collected, washed with dry ethanol, affording 700 mg of the intermediate.

FAB-MS: m/z 103, (20, [M+H]$^+$); PMR (DMSO-d$_6$) δ: 8.38 (b.s., 3H), 7.97 (t, J=6 Hz, 1H), 7.51 (b.s., 4H), 3.45 (m, 2H), 2.92 (m, 2H).

Step II The Intermediate 2-[1-Methyl-4[1-methyl-4[1-methyl-4-aminopyrrole-2-carboxamido]pyrrole-2-carboxamido]pyrrole-2-carboxamido]ethylguanidine Dihydrochloride A solution of 1-methyl-4[1-methyl-4[1-methyl-4-nitropyrrole-2-carboxamido]pyrrole-2-carboxamido]pyrrole-2-carboxylic acid (590 mg) (prepared as reported in Tetrahedron 34,2389–2391,1978) in 20 ml of DMF, 2-aminoethylguanidine dihydrochloride (500 mg), 1-hydroxybenzotriazole hydrate (350 mg), dicycloexylcarbodiimide (880 mg), and sodium bicarbonate (385 mg) was stirred at 70° C. for 4 hours. The solution obtained after filtration was evaporated in vacuo and the residue purified by flash chromatography (methylene chloride/methanol: 8/2) to yield 800 mg of 2-[1-methyl-4[1-methyl-4[1-methyl-4-nitropyrrole-2-carboxamido]pyrrole-2-carboxamido]pyrrole-2-carboxamido]ethylguanidine hydrochloride, which was dissolved in methanol (100 ml), added with 1N hydrochloric acid solution (2 ml) and reduced over Pd catalyst (100 on charcoal) in hydrogen atmosphere (50 psi) in a Parr apparatus. The solution obtained after filtration of the catalyst was evaporated in vacuo and the solid residue washed with dry ethanol to yield 750 mg of the intermediate as a brown powder.

FAB-MS: m/z 469, (15, [M+H]$^+$); PMR (DMSO-d$_6$) δ: 10.38–10.11 (b.s., 4H), 9.98 (s, 1H), 8.28 (b.s., 1H), 8.19 (d, J=1.7 Hz, 1H), 7.73, (b.s., 1H), 7.63 (d, J=1.7 Hz, 1H), 7.60–7.00 (b.s., 4H), 7.28 (d, J=1.7 Hz, 1H), 7.20 (d, J=1.7 Hz, 1H), 7.1 (d, J=1.7 Hz, 1H), 6.92 (d, J=1.7 Hz, 1H), 3.93 (s, 3H), 3.90 (s, 3H), 3.82 (s, 3H), 3.28 (m, 4H).

By analogous procedure and by using the opportune starting materials the following products can be obtained:

3-[1-methyl-4[1-methyl-4[1-methyl-4-aminopyrrole-2-carboxamido]pyrrole-2-carboxamido]pyrrole-2-carboxamido]propioncyanamidine hydrochloride;

3-[1-methyl-4[1-methyl-4[1-methyl-4-aminopyrrole-2-carboxamido]pyrrole-2-carboxamido]pyrrole-2-carboxamido]propionamidoxime hydrochloride;

3-[1-methyl-4[1-methyl-4[1-methyl-4-aminopyrrole-2-carboxamido]pyrrole-2-carboxamido]pyrrole-2-carboxamido]propion-N-methyl-amidine dihydrochloride;

3-[1-methyl-4[1-methyl-4[1-methyl-4-aminopyrrole-2-carboxamido]pyrrole-2-carboxamido]pyrrole-2-carboxamido]propion-N,N'-dimethyl-amidine dihydrochloride;

3-[1-methyl-4[1-methyl-4[1-methyl-4-aminopyrrole-2-carboxamido]pyrrole-2-carboxamido]pyrrole-2-carboxamido]propionamide hydrochloride;

3-[1-methyl-4[1-methyl-4[1-methyl-4-aminopyrrole-2-carboxamido]pyrrole-2-carboxamido]pyrrole-2-carboxamido]propion-N-methylamide hydrochloride; and 3-[1-methyl-4[1-methyl-4[1-methyl-4-aminopyrrole-2-carboxamido]pyrrole-2-carboxamido]pyrrole-2-carboxamido]propionitrile hydrochloride.

Step III The Title Compound

A solution of 250 mg of 1-methyl-4-(α-bromoacrylamido)pyrrole-2-carboxyl chloride (prepared as reported in Example 1 step II) in 15 ml of benzene, was added to a solution of the intermediate obtained from step II (250 mg) and 82 mg of $NaHCO_3$ in 5 ml of $H_2O$. The solution was vigorously stirred for 8 hours at room temperature, then evaporated in vacuo and the crude residue was purified by flash chromatography (methylene chloride/methanol: 8/2) to yield 220 mg of the title compound as a yellow solid.

FAB-MS: m/z 723, (32, [M+H]$^+$); PMR (DMSO-d$_6$) δ: 10.30 (s, 1H), 9.95 (s, 1H), 9.92 (s, 1H), 9.90 (s, 1H), 8.10 (t, J=5.9Hz, 1H), 7.56 (t, J=5.9, 1H), 7.2 (b.s., 4H), 6.9–7.3 (m, 8H), 6.68 (d, J=2.9 Hz, 1H), 6.21 (d, J=2.9 Hz, 1H), 3.85 (s, 3H), 3.84 (s, 3H), 3.83 (s, 3H) 3.80 (s, 3H), 3.30 (b.s., 4H). UV: c=15.3 mg/l(EtOH95%) $\lambda_{MAX}$=312.0 ϵ=48792.

By analogous procedure and by using the opportune starting materials the following products can be obtained:

2-[1-methyl-4[1-methyl-4[1-methyl-4-(α-bromoacrylamido)pyrrole-2-carboxamido]pyrrole-2-carboxamido]pyrrole-2-carboxamido)ethylguanidine hydrochloride;

2-[1-methyl-4[1-methyl-4[1-methyl-4[1-methyl-4-(α-chloro-acrylamido)pyrrole-2-carboxamido]pyrrole-2-carboxamido]pyrrole-2-carboxamido]pyrrole-2-carboxamido]ethylguanidine hydrochloride;

3-(1-methyl-4-(1-methyl-4-(1-methyl-4-(α-bromoacrylamido)pyrrole-2-carboxamido)pyrrole-2-carboxamido)pyrrole-2-carboxamido)propioncyanamidine;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-cyanamidine;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propioncyanamidine;

3-(1-methyl-4-(1-methyl-4-(1-methyl-4-(α-bromoacrylamido) pyrrole-2-carboxamido)pyrrole-2-carboxamido)pyrrole-2-carboxamido)propion-N-methylamidine hydrochloride;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamidine hydrochloride;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N-methylamidine hydrochloride;

3-(1-methyl-4-(1-methyl-4-(1-methyl-4-(α-bromoacrylamido)pyrrole-2-carboxamido)pyrrole-2-carboxamido)pyrrole-2-carboxamido)propion-N,N'-dimethylamidine hydrochloride;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N'-dimethylamidine hydrochloride;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N'-dimethylamidine hydrochloride;

3-(1-methyl-4-(1-methyl-4-(1-methyl-4-(α-bromoacrylamido)pyrrole-2-carboxamido)pyrrole-2-carboxamido)pyrrole-2-carboxamido)propionamidoxime;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionamidoxime;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionamidoxime;

3-(1-methyl-4-(1-methyl-4-(1-methyl-4-(α-bromoacrylamido)pyrrole-2-carboxamido)pyrrole-2-carboxamido)pyrrole-2-carboxamido)propionamide;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionamide;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionamide; and 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamide

EXAMPLE 6

3-[1-Methyl-4[1-methyl-4[1-methyl-4-(α-bromoacrylamido)pyrrole-2-carboxamido]pyrrole-2-carboxamido]pyrrole-2-carboxamido]propionitrile Step I The Intermediate 3-[1-Methyl-4[1-methyl-4[1-methyl-4-aminopyrrole-2-carboxamido]pyrrole-2-carboxamido]pyrrole-2-carboxamido]propionitrile Hydrochloride To a solution of 1 g of distamycin A in 20 ml DMF were added 550 mg of succinic anhydride and 950 mg of $K_2CO_3$. The solution was heated at 60° C. for 3 hours then evaporated to dryness and the crude residue was purified by flash chromatography (methylene chloride/methanol: 9/1) to give 750 g of 3-[1-methyl-4[1-methyl-4[1-methyl-4-formamidopyrrole-2-carboxamido]pyrrole-2-carboxamido] pyrrole-2-carboxamido]propionitrile which was dissolved in 20 ml of methanol and added of 5 ml of HCl 2N. The solution was stirred at room temperature for 2 days, the solvent evaporated in vacuo and the solid residue suspended in 20 ml of ethyl acetate, yielding, after filtration 560 mg of the intermediate.

Step II The Title Compound

To a solution of 80 mg α-bromoacrylic acid in 10 ml of DMF, 57 mg of dicyclohexylcarbodiimide were added. The solution was stirred at room temperature for 20' then added of 110 mg of intermediate obtained from step I and 20 mg of sodium bicarbonate.

The mixture was stirred at room temperature for 8 hours, the solvent was evaporated in vacuo and the crude residue purified by flash chromatography (methylene chloride/methanol: 9/1) to yield 100 mg of the title compound as a yellow solid.

FAB-MS: m/z 571, (10, [M+H]+); PMR (DMSO-d$_6$) δ: 10.29 (s, 1H), 9.96 (s, 1H), 9.92 (s, 1H), 8.32 (t, J=5.9 Hz, 1H), 6.9–7.3 (m, 6H), 6.67 (d, J=2.8 Hz, 1H), 6.22 (d, J=2.8 Hz, 1H), 3.85 (s, 3H), 3.84 (s, 3H), 3.80 (s, 3H), 3.39 (m, 2H), 2.7 (t, J=6.3 Hz, 2H). UV: c=15.1 mg/l(EtOH95%) λ$_{MAX}$=308.4 ε=37068.

By analogous procedure and by using the opportune starting materials the following products can be obtained:

3-[1-methyl-4[1-methyl-4[1-methyl-4[1-methyl-4-(α-bromoacrylamido)pyrrole-2-carboxamido]pyrrole-2-carboxamido]pyrrole-2-carboxamido]pyrrole-2-carboxamido]propionitrile;

3-[1-methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propionitrile;

3-[1-methyl-4[1-methyl-4[1-methyl-4-(α-chloroacrylamido)pyrrole-2-carboxamido]pyrrole-2-carboxamido]pyrrole-2-carboxamido)propion-N-methyl-amidine hydrochloride;

3-[1-methyl-4[1-methyl-4[1-methyl-4-(α-chloroacrylamido)pyrrole-2-carboxamido]pyrrole-2-carboxamido]pyrrole-2-carboxamido]propion-N,N'-dimethyl-amidine hydrochloride;

3-[1-methyl-4[1-methyl-4[1-methyl-4-(α-chloroacrylamido)pyrrole-2-carboxamido]pyrrole-2-carboxamido]pyrrole-2-carboxamido]propionamidoxime;

3-[1-methyl-4[1-methyl-4[1-methyl-4-(α-chloroacrylamido)pyrrole-2-carboxamido)pyrrole-2-carboxamido]pyrrole-2-carboxamido]propioncyanamidine;

3-[1-methyl-4[1-methyl-4[1-methyl-4 (α-chloroacrylamido)pyrrole-2-carboxamido]pyrrole-2-carboxamido]pyrrole-2-carboxamido]propionamide

EXAMPLE 7
3-[1-Methyl-4[1-methyl-4[1-methyl-4[1-methyl-4-(α-bromoacrylamido)pyrrole-2-carboxamido]pyrrole-2-carboxamido]pyrrole-2-carboxamido]pyrrole-2-carboxamido]propionamide Step I The Intermediate 3-[1-Methyl-4[1-methyl-4[1-methyl-4-aminopyrrole-2-carboxamido]pyrrole-2-carboxamido]pyrrole-2-carboxamido]propionamide Hydrochloride To a solution of 1 g of distamycin A in 50 ml of acetonitrile and 50 ml of water, 10 ml of NaOH 1N, were added and the solution was heated at 60° C. for 4 hours. The solvent was evaporated to dryness and the crude residue was purified by flash chromatography (methylene chloride/methanol: 9/1) affording 800 mg of 3-[1-methyl-4[1-methyl-4,1-methyl-4-formamidopyrrole-2-carboxamido]pyrrole-2-carboxamido]pyrrole-2-carboxamido]propionamide which was dissolved in 20 ml of methanol and added of 5 ml of HCl 2N. The reaction was stirred at room temperature for 2 days, the solvent was evaporated in vacuo and the solid residue suspended in 50 ml of ethyl acetate, yielding after filtration 600 mg of the intermediate as a light brown solid.

By analogous procedure and by using the opportune starting material the following product can be obtained:

3-[1-methyl-4[1-methyl-4[1-methyl-4-aminopyrrole-2-carboxamido)pyrrole-2-carboxamido]pyrrole-2-carboxamido]propion-N-methylamide hydrochloride 5 Step II The Title Compound A solution of 260 mg of 1-methyl-4-(α-bromoacrylamido)pyrrole-2-carboxyl chloride (prepared as reported in Example 1 step II) in 25 ml of dioxane, was added to a solution of the intermediate obtained from step II (420 mg) in 25 ml of acetonitrile and 25 ml dioxane and 0.27 ml of triethylamine. The solution was stirred for 1 hour at room temperature, then evaporated in vacuo and the crude residue was purified by flash chromatography (methylene chloride/methanol: 8/2) to yield 220 mg of the title compound as a yellow solid.

FAB-MS: m/z 711, (36, [M+H]+); PMR (DMSO-d$_6$) δ: 10.27 (s, 1H), 9.94 (s, 1H), 9.92 (s, 1H), 9.86 (s, 1H), 7.94 (t, J=5.9 Hz, 1H), 6.8–7.3 (m, 8H), 7.31 (b.s., 1H), 6.79 (b.s., 1H), 6.66 (d, J=2.9 Hz, 1H), 6.21 (d, J=2.9 Hz, 1H), 3.84 (s, 6H), 3.83 (s, 3H), 3.79 (s, 3H), 3.33 (m, 2H), 2.30 (t, J=7.2 Hz, 2H). UV: c=15.1 mg/l(EtOH95%) λ$_{MAX}$=311.0 ε=53146.

By analogous procedure and by using the oppportune starting materials the following products can be obtained:

3-[1-methyl-4[1-methyl-4[1-methyl-4-(α-bromoacrylamido)pyrrole-2-carboxamido]pyrrole-2-carboxamido]pyrrole-2-carboxamido]propionamide;

3-[1-methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propionamide; and 3-[1-methyl-4-[1-methyl-4-[1-methyl-4-(1-methyl-4-(α-bromoacrylamido)pyrrole-2-carboxamido]pyrrole-2-carboxamido]pyrrole-2-carboxamido]pyrrole-2-carboxamido]propion-N-methylamide

EXAMPLE 8
3-[1-Methyl-4[1-methyl-4[1-methyl-4-(α-bromoacrylamido)pyrrole-2-carboxamido]pyrrole-2-carboxamido]pyrrole-2-carboxamido]propion-N-methyl-amidine Hydrochloride Step I The Intermediate 3-[1-methyl-4[1-methyl-4[1-methyl-4-aminopyrrole-2-carboxamido]pyrrole-2-carboxamido]pyrrole-2-carboxamido]propion-N-methyl-amidine Dihydrochloride 1.2 g of 3-[1-methyl-4-[1-methyl-4-[1-methyl-4-nitropyrrole-2-carboxamido]pyrrole-2-carboxamido]pyrrole-2-carboxamido]propionitrile (prepared as reported in J. Med. Chem 22, 1296–1301, 1979) was suspended in dry ethanol and the solution saturated with dry hydrogen chloride After 24 hours at room temperature, the solvent was evaporated in vacuo and the residue treated with two equivalents of solution of methylamine in dry ethanol. After 24 hours at room temperature, the solvent was evaporated in vacuo and the residue purified by flash chromatography yielding 500 mg of 3-[1-methyl-4[1-methyl-4[1-methyl-4-nitropyrrole-2-carboxamido]pyrrole-2-carboxamido)pyrrole-2-carboxamido]propion-N-methylamidine hydrochloride which was dissolved in a mixture of methanol-dioxane-10% hydrochloric acid (4:1:1) and reduced over Pd dioxane-10% hydrochloric acid (4:1:1) and reduced over Pd catalyst (10% on charcoal) in hydrogen atmosphere (50 psi) in a Parr apparatus.

The solution obtained after filtration of the catalyst was evaporated in vacuo, and the solid residue suspended in dry ethanol, and filtered to yield 500 mg of intermediate.

FAB-MS: m/z 468, (40, [M+H]+); PMR (DMSO-d$_6$) δ: 10.20 (s, 3H), 10.18 (s, 1H), 9.98 (s, 1H), 9.65 (m, 1H), 9.20

(s, 1H), 8.63 (s, 1H), 8.25 (t, J=5.8 Hz, 1H), 7.25 (d, J=1.7 Hz, 1H), 7.19 (d, J=1.7 Hz, 1H), 7.11 (d, J=1.7 Hz, 1H) 7.08 (d, J=1.7 Hz, 1H), 7.05 (d, J=1.7 Hz, 1H), 6.91 (d, J=1.7 Hz, 1H), 3.90 (s, 3H), 3.85 (s, 3H), 3.79 (s, 3H), 3.60–3.40 (m, 2H), 2.80 (d, J=6 Hz, 3H), 2.61 (m, 2H).

By analogous procedure and by using the opportune starting materials the following product can be obtained:

- 3-[1-methyl-4[1-methyl-4[1-methyl-4-aminopyrrole-2-carboxamido]pyrrole-2-carboxamido]pyrrole-2-carboxamido]propioncyanamidine hydrochloride;
- 3-[1-methyl-4[1-methyl-4[1-methyl-4-aminopyrrole-2-carboxamido]pyrrole-2-carboxamido]pyrrole-2-carboxamido]propionamidoxime hydrochloride; and
- 3-[1-methyl-4[1-methyl-4[1-methyl-4-aminopyrrole-2-carboxamido]pyrrole-2-carboxamido]pyrrole-2-carboxamido]propion-N,N'-dimethyl-amidine dihydrochloride Step II The Title Compound To a solution of 70 mg α-bromoacrylic acid in 8 ml of DMF, 51 mg of dicyclohexylcarbodiimide were added. The solution as stirred at room temperature, for 20' then added of 108 mg of intermediate obtained from step I and 17 mg of sodium bicarbonate.

The mixture was stirred at room temperature for 10 hours, the solvent was evaporated in vacuo and the crude residue purified by flash chromatography (methylene chloride/methanol: 8/2) to yield 50 mg of the title compound as a yellow solid.

FAB-MS: m/z 600, (20, [M+H]$^+$); PMR (DMSO-d$_6$) δ: 10.28 (s, 1H), 9.93 (s, 1H), 9.88 (s, 1H), 9.4 (b.s. 1H), 9.1 (b.s., 1H), 8.5 (b.s., 1H), 8.18 (t, J=5.9 Hz, 1H), 6.8–7.3 (m, 6H), 6.64 (d, J=2.9 Hz, 1H), 6.18 (d, J=2.9 Hz, 1H), 3.80 (s, 3H), 3.79 (s, 3H), 3.76 (s, 3H), 3.48 (m, 2H), 2.75 (s, 3H), 2.62 (m, 2H).

By analogous procedure and by using the opportune starting materials the following products can be obtained:

- 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-cyanamidine;
- 3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamidine hydrochloride;
- 3-(1-methyl-4-(1-methyl-4-(1-methyl-4-(1-methyl-4-(α-chloro-acrylamido)pyrrole-2-carboxamido)pyrrole-2-carboxamido)pyrrole-2-carboxamido)pyrrole-2-carboxamido)propion-N-methylamidine hydrochloride;
- 3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N'-dimethylamidine hydrochloride; and
- 3-(1-methyl-4-(1-methyl-4-(1-methyl-4-(α-bromoacrylamido)pyrrole-2-carboxamido)pyrrole-2-carboxamido)pyrrole-2-carboxamido)propionamidoxime.

EXAMPLE 9

3-[1-Methyl-4[1-methyl-4[1-methyl-4[1-methyl-4-(α-bromo-acrylamido)pyrrole-2-carboxamido]pyrrole-2-carboxamido]pyrrole-2-carboxamido]pyrrole-2-carboxamido]propionitrile To a solution of 350 mg of 3-[1-methyl-4[1-methyl-4[1-methyl-4-[1-methyl-4-(α-bromoacrylamido)pyrrole-2-carboxamido]pyrrole-2-carboxamido]pyrrole-2-carboxamido]pyrrole-2-carboxamido]propionamidine hydrochloride (prepared as reported in WO 90/11277) in 20 ml of DMF, were added 120 mg of succinic anhydride and 165 mg of K$_2$CO$_3$. The solution was heated at 60° C. for 3 hours then the solvent evaporated under reduced pressure and the crude residue was purified by flash chromatography (methylene chloride/methanol: 95/5) to yield 150 mg of the title compound as a pale yellow solid.

FAB-MS: m/z 693, (100, [M+H]$^+$); PMR (DMSO-d6) δ: 10.32 (s, 1H) 10.00 (s, 1H), 9.97 (s, 1H), 9.95 (s, 1H) 8.36 (t, J=5.9 Hz, 1H), 6.9–7.3 (m, 8H), 6.70 (d, J=2.7 Hz, 1H), 6.25 (d, J=2.7 Hz, 1H), 3.88 (s, 6H), 3.87 (s, 3H), 3.60 (s, 3H), 3.42 (m, 2H), 2.75 (t, J=6.5 Hz, 2H). UV: c=20.3 mg/l(EtOH95%) λ$_{MAX}$=312.6 ε=45606.

By analogous procedure and by using the opportune starting materials the following products can be obtained:

- 3-[1-methyl-4[1-methyl-4[1-methyl-4-(α-bromoacrylamido)pyrrole-2-carboxamido]pyrrole-2-carboxamido]pyrrole-2-carboxamido]propionitrile; and
- 3-[1-methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propionitrile.

EXAMPLE 10

3-[1-Methyl-4[1-methyl-4[1-methyl-4[1-methyl-4-(α-chloroacrylamido)pyrrole-2-carboxamido]pyrrole-2-carboxamido]pyrrole-2-carboxamido]pyrrole-2-carboxamido]propion-N-methyl-amidine Hydrochloride To a solution of the intermediate prepared as reported in Example 2, step I, and 100 mg of NaHCO$_3$ in 15 ml of water, 395 mg of 1-methyl-4-(α-chloroacrylamido)pyrrole-2-carboxyl chloride in 15 ml of benzene were added. The reaction was stirred vigorously for 4 hours, then the solvent was evaporated under vacuum and the crude residue purified by flash chromatography (methylene chloride/methanol: 8/2) to yield 135 mg of the title compound as a yellow powder.

FAB-MS: m/z 678, (45, [M+H]$^+$); PMR (DMSO-d6) δ: 10.29 (s, 1H), 9.96 (s, 1H), 9.92 (s, 1H), 9.89 (s, 1H), 8.9 (b.s., 3H), 8.19 (t, J=5.9 Hz, 1H), 6.9–7.3 (m, 8H), 6.37 (d, J=2.2 Hz, 1H), 5.99 (d, J=2.2 Hz, 1H), 3.84 (s, 6H), 3.83 (s, 3H), 3.79 (s, 3H), 3.48 (m, 2H), 2.78 (s, 3H), 2.59 (m, 2H). UV: c=18.5 mg/l(EtOH95%) λ$_{MAX}$=312.6 ε=44232.

By analogous procedure and by using the opportune starting materials the following products can be obtained:

- 3-[1-methyl-4[1-methyl-4[1-methyl-4[1-methyl-4-(α-bromoacrylamido)pyrrole-2-carboxamido]pyrrole-2-carboxamido]pyrrole-2-carboxamido]pyrrole-2-carboxamido]propion-N-methyl-amidine hydrochloride; and
- 3-(1-methyl-4[1-methyl-4[1-methyl-4-(α-bromoacrylamido)pyrrole-2-carboxamido)pyrrole-2-carboxamido]pyrrole-2-carboxamido]pyrrole-2-carboxamido]propion-N-methyl-amidine hydrochloride

What is claimed is:
1. A compound of formula:

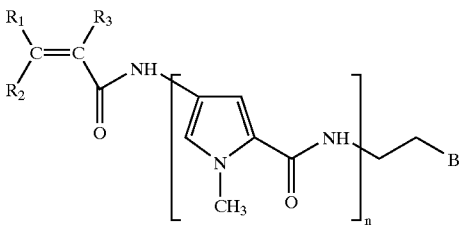

wherein:
n is 2, 3 or 4;
$R_1$ and $R_2$ are selected, each independently, from: hydrogen, halogen, and $C_1$–$C_4$ alkyl;
$R_3$ is hydrogen or halogen;
B is selected from:

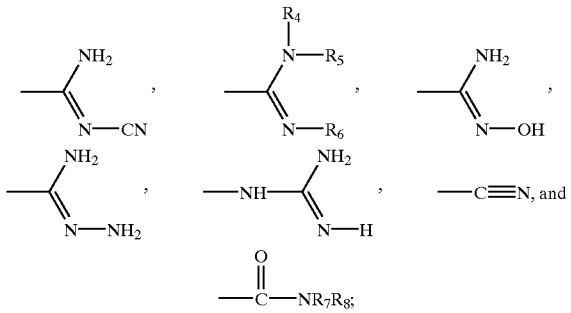

wherein $R_4$, $R_5$, $R_6$, $R_7$, and $R_8$ are, each independently, hydrogen or $C_1$–$C_4$ alkyl, with the proviso that at least one of $R_4$, $R_5$ and $R_6$ is $C_1$–$C_4$ alkyl; or a pharmaceutically acceptable salt thereof.

2. A compound as defined in claim 1, wherein:
n is 3 or 4;
$R_1$ and $R_2$ are hydrogen;
$R_3$ is chlorine or bromine;
B is selected from:

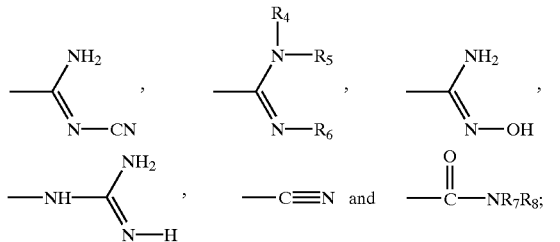

wherein $R_4$, $R_5$, $R_6$, $R_7$, and $R_8$ are, each independently, hydrogen or methyl, with the proviso that at least one of $R_4$, $R_5$ and $R_6$ is methyl.

3. A compound of claim 1, wherein n is 4, $R_1$ and $R_2$ are each hydrogen, $R_3$ is bromine and B is the group —NH—C(NH$_2$)=NH.

4. A compound as defined in claim 1, selected from:
3-(1-methyl-4-(1-methyl-4-(1-methyl-4-(α-bromoacrylamido) pyrrole-2-carboxamido) pyrrole-2-carboxamido) pyrrole-2-carboxamido) propioncyanamidine;

3-(1-methyl-4-(1-methyl-4-(1-methyl-4-(1-methyl-4-(α-bromoacrylamido)pyrrole-2-carboxamido) pyrrole-2-carboxamido) pyrrole-2-carboxamido)pyrrole-propioncyanamidine;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propioncyanamidine;

3-1-methyl-4-(1-methyl-4-(1-methyl-4-(α-bromoacrylamido)pyrrole-2-carboxamido)pyrrole-2-carboxamido)pyrrole-2-carboxamido)propion-N-methylamidine;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrroie-2-carboxamido)propion-N-methylamidine;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N-methylamidine;

3-1-methyl-4-(1-methyl-4-(1-methyl-4-(α-bromoacrylamido)pyrrole-2-carboxamido)pyrrole-2-carboxamido)pyrrole-2-carboxamido)propion-N,N'-dimethylamidine;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N'-dimethylamidine;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N,N'-dimethylamidine;

3-(1-methyl-4-(1-methyl-4-(1-methyl-4-(α-bromoacrylamido)pyrrole-2-carboxamido)pyrrole-2-carboxamido)pyrrole-2-carboxamido) propionamidoxime;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)

3-(1-methyl-4-(1-methyl-4-(1-methyl-4-(1-methyl-4-(α-chloroacrylamido) pyrrole-carboxamido)pyrrole-2-carboxamido)pyrrole-2-carboxamido)pyrrole-2-carboxamido)propionamidoxime;

2-(1-methyl-4-(1-methyl-4-(1-methyl-4-(α-bromoacrylamido)pyrrole-2-carboxamido)pyrrole-2-carboxamido)pyrrole-2-carboxamido) ethylguanidine;

2-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)ethylguanidine;

2-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)ethylguanidine;

3-(1-methyl-4-(1-methyl-4-(1-methyl-4-(α-bromoacrylamido)pyrrole-2-carboxamido)pyrrole-2-carboxamido)pyrrole-2-carboxamido)propionitrile;

3-(1-methyl-4-(1-methyl-4-(l1-methyl-4-(1-methyl-4-(α-bromoacrylamido) pyrrole-2-carboxamido)pyrrole-2-carboxamido)pyrrole-2-carboxamido)pyrrole-2-carboxamido)propionitrile;

3-(1-methyl-4-(1-methyl-4-(1-methyl-4-(1-methyl-4-(α-chloroacrylamido)pyrrole-2-carboxamido)pyrrole-2- carboxamido)pyrrole-2-carboxamido)pyrrole-2-carboxamido)propionitrile;

3-(1-methyl-4-(1-methyl-4-(1-methyl-4-(α-bromoacrylamido)pyrrole-2-carboxamido)pyrrole-2-carboxamido)pyrrole-2-carboxamido)propionamide;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propionamide;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propionamide;

3-(1methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N-methylamide;

3-1-methyl-4-(1-methyl-4-(1-methyl-4-(α-bromoacrylamido)pyrrole-2-carboxamido)pyrrole-2-carboxamido)pyrrole-2-carboxamido)propion-N,N-dimethylamidine;

3-(1-methyl-4-(1-methyl-4-(1-methyl-4-(1-methyl-4-(α-bromoacrylamido)pyrrole-2-carboxamido)pyrrole-2-carboxamido)pyrrole-2-carboxamido)pyrrole-2-carboxamido)propion-N,N-dimethylamidine;

3-(1-methyl-4-(1-methyl-4-(1-methyl-4-(1-methyl-4-(α-chloroacrylamido)pyrrole-2-carboxamido)pyrrole-2-carboxamido)pyrrole-2-carboxamido)pyrrole-2-carboxamido)propion-N, N-dimethylamidine;

3-(1-methyl-4-(1-methyl-4-(1-methyl-4-(α-chloroacrylamido)pyrrole-2-carboxamido)pyrrole-2-carboxamido)pyrrole-2-carboxamido)propion-N-methyl-amidine;

3-1-methyl-4-(1-methyl-4-(1-methyl-4-(α-chloroacrylamido)pyrrole-2-carboxamido)pyrrole-2-carboxamido)pyrrole-2-carboxamido)propion-N,N'-dimethyl-amidine;

3-(1-methyl-4-(1-methyl-4-(1-methyl-4-(α-chloroacrylamido)pyrrole-2-carboxamido)pyrrole-2-carboxamido)pyrrole-2-carboxamido) propionamidoxime;

3-(1-methyl-4-(1-methyl-4-(1-methyl-4-(α-chloroacrylamido)pyrrole-2-carboxamido)pyrrole-2-carboxamido)pyrrole-2-carboxamido) propioncyanamidine; and 3-(1-methyl-4-(1-methyl-4-(1-methyl-4-(α-chloroacrylamido)pyrrole-2-carboxamido)pyrrole-2-carboxamido)pyrrole-2-carboxamido)propionamide;

and a pharmaceutically acceptable salt thereof.

5. A pharmaceutical composition comprising an acceptable carrier, together with a compound according to claim 1 in an amount effective to inhibit growth of tumor cells.

6. A process for producing a compound as defined in claim 1, which process comprises:

(a) reacting a compound of formula:

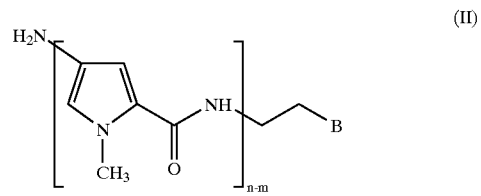

(II)

wherein:

n is 2, or 3 or 4;

m is 0 or 1;

B is selected from:

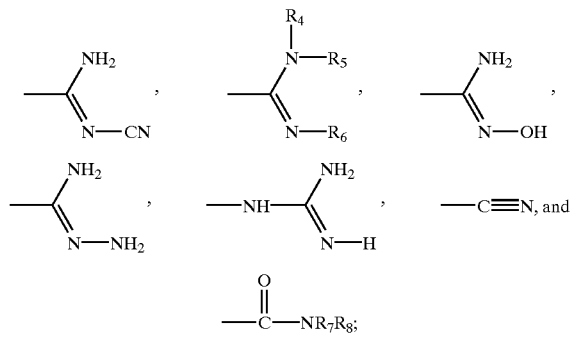

wherein $R_4$, $R_5$, $R_6$, $R_7$, and $R_8$ are, each independently, hydrogen or $C_1$–$C_4$ alkyl, with the proviso that at least one of $R_4$, $R_5$, $R_6$ is $C_1$–$C_4$ alkyl; with a compound of formula:

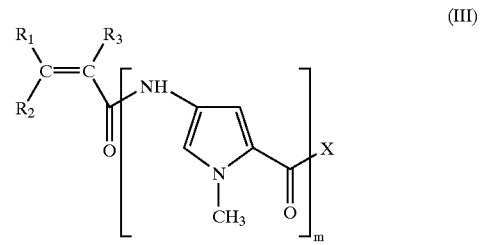

(III)

wherein: $R_1$ and $R_2$ are selected, each independently, from: hydrogen, halogen, and $C_1$–$C_4$ alkyl; $R_3$ is hydrogen or halogen; X is hydroxy or a leaving group; and m has the above reported meanings;

for a time and under conditions effective to produce a compound of formula I, and optionally, converting a compound of formula (I) into a pharmaceutically acceptable salt thereof;

and isolating the compound of formula I or the pharmaceutically acceptable salt thereof.

7. A process for producing a compound as defined in claim 1 wherein B is —C≡N, which process comprises:

(a) reacting a compound of formula:

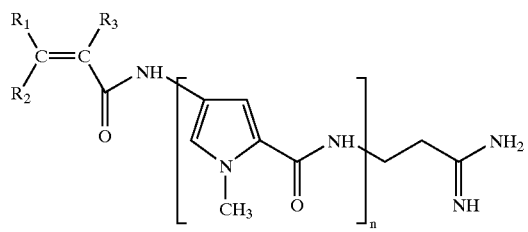

(IV)

wherein n is 2 or 3 or 4; and $R_1$ and $R_2$ are selected, each independently, from: hydrogen, halogen, and $C_1$–$C_4$ alkyl; $R_3$ is hydrogen or halogen;

with succinic anhydride for a time and under conditions effective to produce a compound of formula I, and optionally, converting a compound of formula (I) into a pharmaceutically acceptable salt thereof;

and isolating the compound of formula I or the pharmaceutically acceptable salt thereof.

8. A method of inhibiting growth of a tumor in a human or animal body in need of such inhibition, comprising administering to said human or animal body a tumor growth inhibiting effective amount of a compound of claim 1 for a time and under conditions effective to inhibit growth of said tumor.

9. A method of treating a mammal afflicted with a tumor growth, comprising administering to said mammal an antitumor effective amount of a compound of claim 1 for a time and under conditions effective to inhibit growth of said tumor.

10. A method of inhibiting growth of tumor cells, comprising contacting the tumor cells with a growth inhibiting effective amount of a compound of claim 1 for a time and under conditions effective to inhibit growth of said tumor cells.

* * * * *